(12) United States Patent
Bailey et al.

(10) Patent No.: US 12,070,341 B2
(45) Date of Patent: Aug. 27, 2024

(54) PATIENT SUPPORT MECHANISM FOR A PORTABLE MEDICAL SCANNER

(71) Applicant: Siemens Medical Solutions USA, Inc., Malvern, PA (US)

(72) Inventors: Eric M. Bailey, North Hampton, NH (US); Andrew Tybinkowski, Topsfield, MA (US); Charles Landry, Seabrook, NH (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 633 days.

(21) Appl. No.: 17/283,305

(22) PCT Filed: Oct. 24, 2019

(86) PCT No.: PCT/US2019/057751
§ 371 (c)(1),
(2) Date: Apr. 7, 2021

(87) PCT Pub. No.: WO2020/106402
PCT Pub. Date: May 28, 2020

(65) Prior Publication Data
US 2021/0386386 A1    Dec. 16, 2021

Related U.S. Application Data

(60) Provisional application No. 62/769,094, filed on Nov. 19, 2018.

(51) Int. Cl.
*A61B 6/00* (2024.01)
*A61B 6/04* (2006.01)

(52) U.S. Cl.
CPC .......... *A61B 6/0407* (2013.01); *A61B 6/4405* (2013.01)

(58) Field of Classification Search
CPC ........... A61B 6/00; A61B 6/04; A61B 6/0407; A61B 6/4405; A61G 2200/54; A61G 13/10; A61G 13/12; A61G 13/1255
See application file for complete search history.

(56) References Cited

U.S. PATENT DOCUMENTS 5,233,713 A * 8/1993 Murphy ............... A61G 13/121
5/636
8,750,451 B2    6/2014 Tybinkowski et al.
(Continued)

FOREIGN PATENT DOCUMENTS

CN    2236818 Y    10/1996
CN    104869908 A    8/2015
(Continued)

*Primary Examiner* — Fredrick C Conley

(57) ABSTRACT

A patient support mechanism that supports a patient during scanning of the patient by a medical scanner. The support mechanism includes a shoulder support rotatably attached to a head support. The head support receives the patient's head and the shoulder support receives an upper portion of the patient's body wherein the shoulder support includes a downwardly extending attachment device. The support mechanism also includes an attachment mechanism having a post section that is attached to the medical scanner. Further, the attachment mechanism includes a bracket element for receiving the attachment device wherein the shoulder support is attached to the bracket element by positioning the shoulder support above the bracket element and moving the shoulder support downward to attach the attachment device to the bracket element while the patient is lying in bed.

23 Claims, 4 Drawing Sheets

(56) References Cited

U.S. PATENT DOCUMENTS

| | | | |
|---|---|---|---|
| 2002/0032927 A1* | 3/2002 | Dinkler | A61G 13/12 |
| | | | 5/601 |
| 2004/0055089 A1 | 3/2004 | Dinkler et al. | |
| 2005/0135560 A1* | 6/2005 | Dafni | A61B 6/56 |
| | | | 378/101 |
| 2008/0178893 A1 | 7/2008 | Kusner et al. | |
| 2010/0205740 A1* | 8/2010 | Tybinkowski | G01N 23/046 |
| | | | 5/601 |
| 2012/0124748 A1* | 5/2012 | Soto | A61G 13/101 |
| | | | 5/640 |
| 2012/0321051 A1 | 12/2012 | Jarva | |
| 2015/0374320 A1 | 12/2015 | Suuronen et al. | |
| 2016/0374630 A1 | 12/2016 | Smith et al. | |
| 2023/0320677 A1* | 10/2023 | Smith | A61B 6/4405 |
| | | | 378/4 |

FOREIGN PATENT DOCUMENTS

| | | |
|---|---|---|
| CN | 108294776 A | 7/2018 |
| JP | S6443235 A | 2/1989 |
| WO | 2017039522 A1 | 3/2017 |

\* cited by examiner

PATIENT SUPPORT MECHANISM FOR A PORTABLE MEDICAL SCANNER

PRIORITY CLAIM

This application is a U.S. National Phase Application of PCT/US2019/057751 filed on Oct. 24, 2019, which claims the benefit of U.S. Provisional Application No. 62/769,094 filed on Nov. 19, 2018, which is incorporated herein by reference in its entirety and to which this application claims the benefit of priority.

TECHNICAL FIELD

Aspects of the present invention relate to a patient support mechanism for a portable medical scanner, and more particularly, to a patient support mechanism that is attached to the medical scanner and includes a shoulder support rotatably attached to a head support wherein the shoulder support is attached by positioning the shoulder support above a bracket element of the patient support mechanism and moving the shoulder support downward to attach the shoulder support to the bracket element while the patient is lying in bed.

BACKGROUND

Portable imaging systems, such as portable computer tomography (CT) imaging systems, may be used to scan a patient to generate medical images while the patient is in bed. Support apparatus is often needed to support the patient when performing bedside imaging to ensure safety, patient comfort, image quality and to reduce motion during imaging to avoid image blur. These reasons are often competitive with each other.

The support apparatus used with the imaging systems is mounted to the patient bed. Due to the relatively large variety of make and model patient beds, the support apparatus has to be able to accommodate many differently configured beds. In addition, the mounting of the support apparatus often requires a substantial amount of manipulation of the patient, bed, and attached life support equipment, which may be hazardous for the patient. Further, the support apparatus may be of a one-piece design that does not sufficiently conform to patient anatomy and thus is not comfortable.

SUMMARY OF THE INVENTION

A patient support mechanism is disclosed that supports a patient scanning of the patient by a medical scanner. The support mechanism includes a shoulder support rotatably attached to a head support. The head support receives the patient's head and the shoulder support receives an upper portion of the patient's body wherein the shoulder support includes a downwardly extending attachment device. The support mechanism also includes an attachment mechanism having a post section that is attached to the medical scanner. Further, the attachment mechanism includes a bracket element for receiving the attachment device wherein the shoulder support is attached to the bracket element by positioning the shoulder support above the bracket element and moving the shoulder support downward to attach the attachment device to the bracket element while the patient is lying in bed.

Those skilled in the art may apply the respective features of the present invention jointly or severally in any combination or sub-combination.

BRIEF DESCRIPTION OF THE DRAWINGS

The exemplary embodiments of the invention are further described in the following detailed description in conjunction with the accompanying drawings, in which:

FIGS. 5A-5B depict alternate embodiments of the support mechanism wherein FIG. 5A depicts the support mechanism including an image quality phantom and FIG. 5B depicts the support mechanism including a body board sized for pediatric or neonatal patients.

To facilitate understanding, identical reference numerals have been used, where possible, to designate identical elements that are common to the figures. The figures are not drawn to scale.

DETAILED DESCRIPTION

Figure 1:
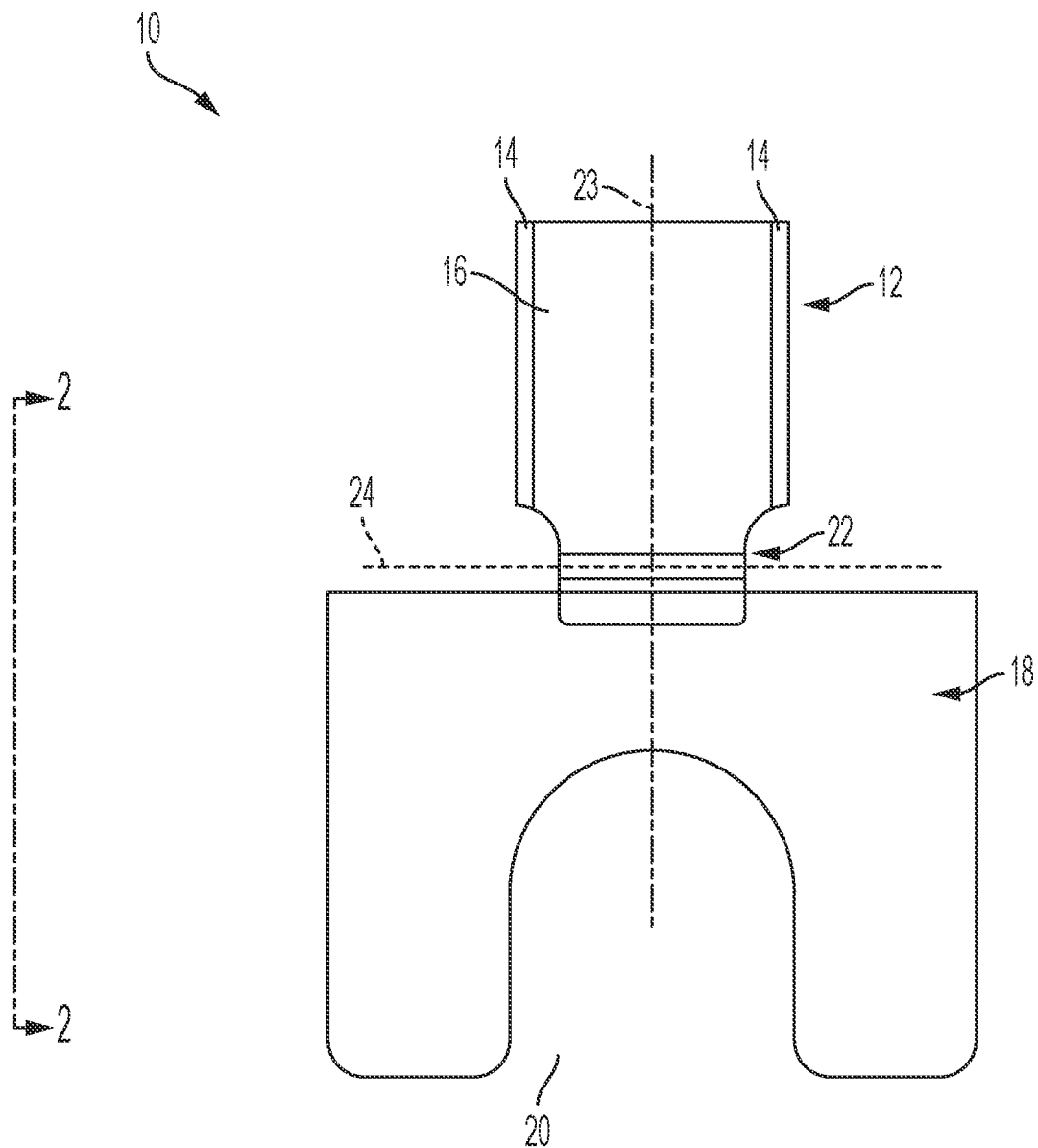
FIG. 1 is a top view of a patient support mechanism in accordance with an aspect of the invention.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Referring to FIG. 1, a top view of a patient support mechanism 10 in accordance with an aspect of the invention is shown. The support mechanism 10 includes a head support element 12 having a curved wall 14 that forms a concave portion 16 for receiving a patient's head. The support mechanism 10 also includes a substantially flat shoulder support element 18 having a cutout portion 20 for accommodating the patient's head when the patient is lying on a patient bed. The head 12 and shoulder 18 supports are aligned along a center axis 23 of the support mechanism 10. The support mechanism 10 further includes an attachment mechanism 22 that receives the shoulder support 18 and enables rotation of either the head support 12 or shoulder support 18, or both, about a second axis 24 oriented transverse to the center axis 23.

In an embodiment, the head support 12 may be fabricated from a different material than the shoulder support 18. This enables the selection of materials suitable for each support 12, 18. For example, the head support 12 may be fabricated from a material that is translucent to X-rays whereas the shoulder support 18 may be fabricated from a material that is less expensive than that used for the head support 12, thus reducing costs. In addition, the shoulder support 18 may be fabricated from a material that is stronger than that used for the head support 12.

Figure 2:
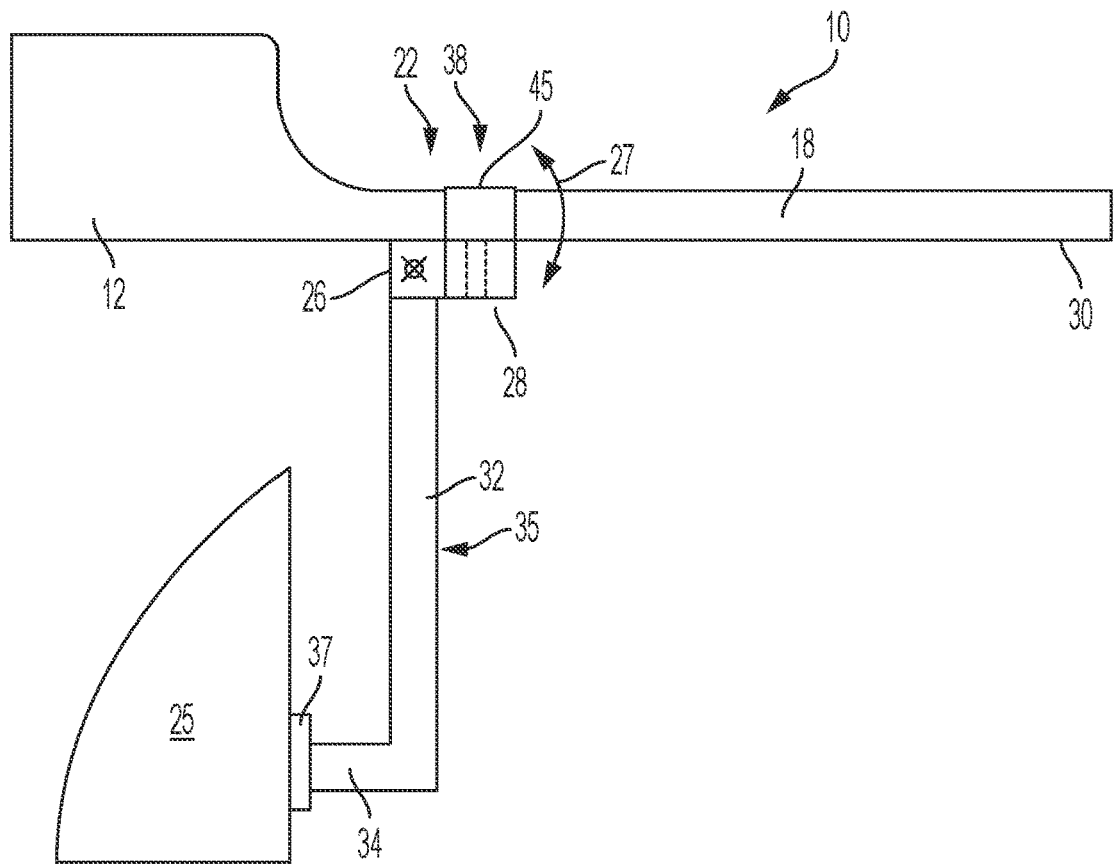
FIG. 2 is a side view of the patient support mechanism along view line 2-2 of FIG. 1.

Referring to FIG. 2, a side view of the support mechanism 10 along view line 2-2 of FIG. 1 is shown. The attachment mechanism 22 includes a rotating element portion 26 located under the head support 12. The attachment mechanism 22 further includes a bracket portion 28 located adjacent the rotating element 26. A second end 38 of the shoulder support 18 is attached to the bracket portion 28 via a pin element 40 as will be described. The rotating element 26 enables rotation of the shoulder support 18 about the second axis 24 in either clockwise or counterclockwise directions 27 in order to accommodate an orientation of a patient's bed or mattress. In an aspect of the invention, the head support 12 is held stationary or locked in place during rotation of the shoulder support 18. For example, the shoulder support 18 may be rotated downward such that a first end 30 contacts the mattress to compensate for mattress sag that occurs due to shifting patient weight as the patient is pulled across the mattress and onto the shoulder support 18. Contact between the first end 30 and the mattress supports the shoulder support 18 and reduces the amount of stress that the support mechanism 10 is subjected to, thereby reducing the likelihood of damage. Alternatively, the shoulder support 18 may be rotated upward in order to accommodate a height of the patient bed, for example. In addition, rotation of the shoulder support 18 maintains patient comfort and reduces an amount of the patient's breathing motion that is transferred to the patient's head, thus substantially reducing or eliminating artifacts in the generated images due to head motion. Alternatively, the head support 12 may be rotatable or both the head 12 and shoulder 18 supports may be rotatable. In addition, a detent mechanism may be used to orient the head support 12 in a desired position.

The attachment mechanism 22 also includes a post member 35 having a substantially vertical post section 32 that extends downward from the rotating element 26. The post member 35 also includes a transverse attachment section 34, oriented transverse to the vertical post section 32, that extends toward a medical scanner 25 to form a substantially reverse "L" configuration. In accordance with an aspect of the invention, a scanner bracket 37 is removably attached to the medical scanner 25. The transverse section 34 is removably attached to the scanner bracket 37 thereby attaching the attachment mechanism 22, and thus the support mechanism 10, to the medical scanner 25. Thus, by mounting the support mechanism 10 to the medical scanner 25 rather than a patient bed, the disadvantages associated with having to accommodate many differently configured beds and bed adapters in order to attach the support mechanism 10 are avoided. The head support 12 is removably attached to the rotating element 26 by fasteners, for example. This enables attachment of a head support 12 sized to fit a patient's head size. In an embodiment, the head support 12 may be configured in at least three sizes such as adult, pediatric and neonatal sizes.

Figure 3:
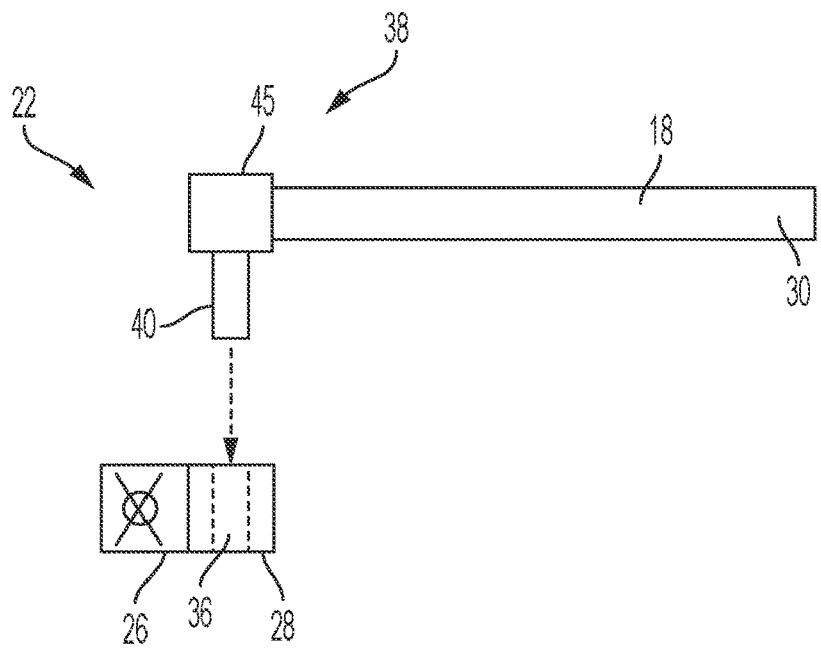
FIG. 3 is an exploded side view of an attachment mechanism for the patient support mechanism.

Referring to FIG. 3, an exploded side view of the attachment mechanism 22 is shown. In an embodiment, the rotating element 26 may be a hinge or other element that enables rotation. The bracket portion 28 includes a bracket hole 36. The second end 38 of the shoulder support 18 includes a pin holder 45 having a removable downwardly extending pin element 40 or other removable attachment device that is inserted into the bracket hole 36 to removably attach the shoulder support 18 to the bracket portion 28. The shoulder support 18 is attached to the bracket portion 28 by positioning the shoulder support 18 in an elevated position above the bracket portion 28, aligning the pin element 40 with the bracket hole 36, and moving the shoulder support 18 downward from the elevated position and toward the bracket portion 28 until the pin element 40 is inserted into the bracket hole 36. It understood that more than one pin element 40 and associated bracket hole 36 may be used. In addition, the pin element 40 and associated bracket hole 36 may have a round cross-section or other suitable shape such as oval, arcuate, polygonal and others. Alternatively, other removable attachment devices may be used to removably attach the shoulder support 18 to the bracket portion 28 such as at least one mechanical fastener or magnet arrangement, for example.

Figure 4:
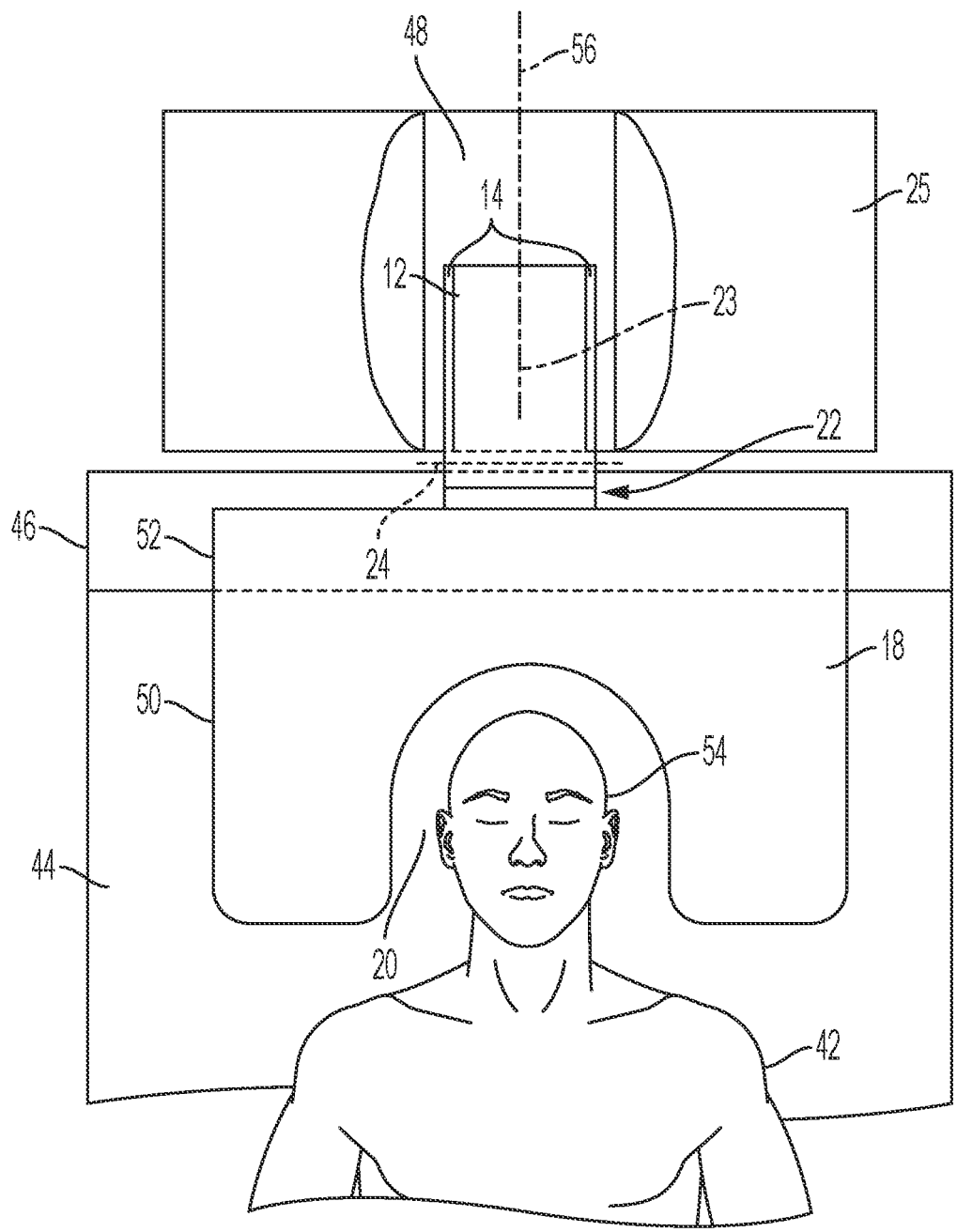
FIG. 4 shows the support mechanism attached to a medical scanner and depicts a patient lying on a mattress of a patient bed.

Referring to FIG. 4, the support mechanism 10 is shown attached to the medical scanner 25 and depicts a patient 42 lying on a mattress 44 of a patient bed 46. The bed 46 may be any type of conventional patient bed or other type of patient-supporting platform found in a health care facility, for example. First 50 and second 52 upper portions of the mattress 44 and bed 46, respectively, are located underneath the shoulder support 18 and a portion of the patient's head 54 is located within the cutout 20. The medical scanner 25 includes a patient opening or bore 48 that receives the head support 12. In an embodiment, the medical scanner 25 may be a portable medical scanner such as a portable CT imaging system having an X-ray source and X-ray detector and various electronic hardware and software for generating CT scans wherein the CT imaging system is translated and the patient 42 remains stationary. Alternatively, the portable medical scanner 25 may be a magnetic resonance imaging (MRI) scanner, positron emission tomography (PET) scanner, single-photon emission computerized tomography (SPECT) scanner, an X-ray scanner, or use surgery or interventional technologies.

As previously described, the shoulder support 18 is attached to the bracket portion 28 by positioning the shoulder support 18 in an elevated position above the bracket portion 28 and moving the shoulder support 18 downward from the elevated position toward the bracket portion 28 until the pin element 40 is inserted into the bracket hole 36. The downward movement of the shoulder support 18 and cutout 20 allow installation of the shoulder support 18 around the head 54 of a patient 42 who is already lying on the bed 46 without interfering with the patient 42 or life support equipment being used by the patient 42. Insertion of the pin element 40 into the bracket hole 36 aligns the center axis 23 of the head support 12 with a center axis 56 of the patient bore 48. In order to generate images of the patient's head, an upper portion of the patient 42 is then pulled onto the shoulder support 18 and the patient's head 54 is positioned in the head support 12. This enables consistent and accurate positioning of the patient 42 relative to the medical scanner 25 and enables scanning of the head 54 while the patient 42 remains on the bed 46. In an aspect of the invention, at least one electric motor may used to move and/or rotate the support mechanism 10 for suitable placement relative to the bore 48.

Figure 5A:
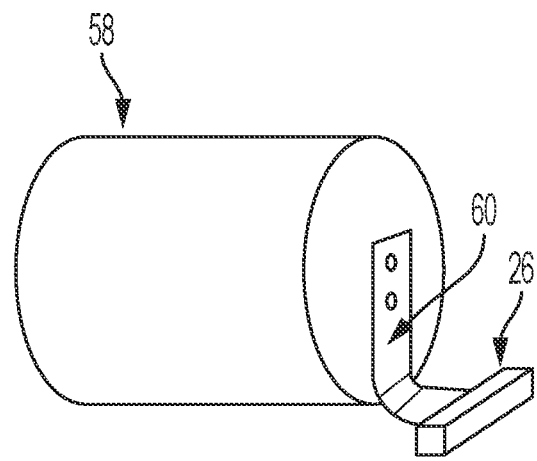
Figure 5B:
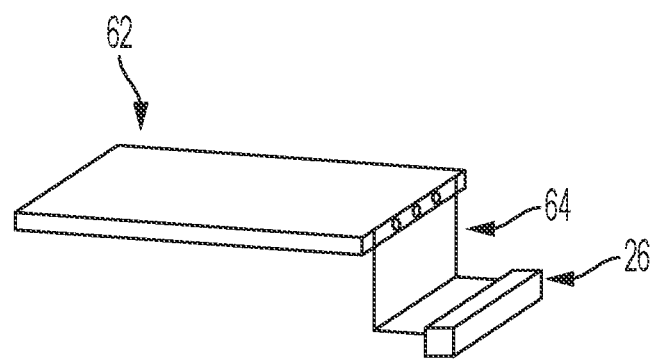

Referring to FIGS. 5A-5B, alternate embodiments of the support mechanism 10 are shown. Referring to FIG. 5A, the head support 12 may be replaced by an image quality phantom 58 such as a CT (or other modality) image quality phantom. In particular, the phantom 58 includes a substantially L-shaped bracket 60 that may be removably attached to the rotating element 26. Referring to FIG. 5B, the head support 12 may be replaced by a body board 62 fabricated from an X-ray translucent material, for example, that is sized for pediatric or neonatal patients. The body board 62 includes a bracket 64 that may be removably attached to the rotating element. Alternatively, the head support 12 may be replaced with a support element that is shaped to accommodate other body parts such as an arm, leg, foot and others or a baby's body.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A patient support mechanism that supports a patient during scanning of the patient by a medical scanner, comprising:
    a shoulder support rotatably attached to a head support, wherein the head support receives the patient's head and the shoulder support receives an upper portion of the patient's body and wherein the shoulder support includes a downwardly extending attachment device; and
    an attachment mechanism having a post section attached to the medical scanner wherein the attachment mechanism includes a bracket element that receives the attachment device and wherein the attachment mechanism orients the shoulder and head supports in a position that enables scanning of the patient by the medical scanner.

2. The mechanism according to claim 1, wherein the shoulder support includes a cutout that receives the patient's head.

3. The mechanism according to claim 1, wherein the attachment device is a pin element.

4. The mechanism according to claim 1, wherein the shoulder support is rotatably attached to the head support by a hinge.

5. The mechanism according to claim 1, wherein the head support is fabricated from an X-ray translucent material.

6. The mechanism according to claim 1, wherein the head support is received by a patient bore of the medical scanner.

7. The mechanism according to claim 1, wherein the medical scanner is a portable medical scanner.

8. The mechanism according to claim 1, wherein the bracket element receives the attachment device as the patient is lying in bed.

9. A patient support mechanism that supports a patient during scanning of the patient by a medical scanner, comprising:
    a shoulder support rotatably attached to a head support, wherein the head support receives the patient's head and the shoulder support receives an upper portion of the patient's body and wherein the shoulder support includes a downwardly extending attachment device; and
    an attachment mechanism having a post section attached to the medical scanner wherein the attachment mechanism further includes a bracket element that receives the attachment device wherein the attachment mechanism orients the shoulder and head supports in a position that enables scanning of the patient by the medical scanner and wherein the shoulder support is attached to the bracket element by positioning the shoulder support above the bracket element and moving the shoulder support downward to attach the attachment device into the bracket element.

10. The mechanism according to claim 9, wherein the shoulder support includes a cutout that receives the patient's head.

11. The mechanism according to claim 9, wherein the attachment device is a pin element.

12. The mechanism according to claim 9, wherein the shoulder support is rotatably attached to the head support by a hinge.

13. The mechanism according to claim 9, wherein the head support is fabricated from an X-ray translucent material.

14. The mechanism according to claim 9, wherein the head support is received by a patient bore of the medical scanner.

15. The mechanism according to claim 9, wherein the medical scanner is a portable medical scanner.

16. The mechanism according to claim 9, wherein the bracket element receives the attachment device as the patient is lying in bed.

17. A method of supporting a patient during scanning of the patient by a medical scanner, comprising:
    providing a shoulder support rotatably attached to a head support, wherein the head support receives the patient's head and the shoulder support receives an upper portion of the patient's body;
    providing a downwardly extending attachment device that extends from the shoulder support;
    providing an attachment mechanism having a post section attached to the medical scanner;
    providing a bracket element on the attachment mechanism;
    positioning the shoulder support above the bracket element;
    moving the shoulder support downward toward the patient to attach the attachment device into the bracket wherein the attachment mechanism orients the shoulder and head supports in a position that enables scanning of the patient by the medical scanner.

18. The method according to claim 17, wherein the shoulder support includes a cutout that receives the patient's head.

19. The method according to claim 17, wherein the attachment device is a pin element.

20. The method according to claim 17, wherein the shoulder support is rotatably attached to the head support by a hinge.

21. The method according to claim 17, wherein the head support is fabricated from an X-ray translucent material.

22. The method according to claim 17, wherein the medical scanner is a portable medical scanner.

23. The mechanism according to claim 17, wherein the bracket element receives the attachment device as the patient is lying in bed.

* * * * *